(12) United States Patent
Bacher et al.

(10) Patent No.: US 10,299,855 B2
(45) Date of Patent: May 28, 2019

(54) MEDICAL COAGULATION INSTRUMENT

(71) Applicant: Karl Storz SE & Co. KG, Tuttlingen (DE)

(72) Inventors: Uwe Bacher, Tuttlingen (DE); Rainer Hermle, Gosheim (DE); Andreas Efinger, Rietheim (DE); Hans-Peter Eisele, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 929 days.

(21) Appl. No.: 14/610,314

(22) Filed: Jan. 30, 2015

(65) Prior Publication Data

US 2015/0141991 A1    May 21, 2015

Related U.S. Application Data

(63) Continuation-in-part of application No. 12/816,810, filed on Jun. 16, 2010, now Pat. No. 8,974,455.

(30) Foreign Application Priority Data

Jun. 16, 2009   (DE) .......................... 10 2009 025405

(51) Int. Cl.
 *A61B 18/14* (2006.01)
 *A61B 18/12* (2006.01)

(52) U.S. Cl.
 CPC .... *A61B 18/1482* (2013.01); *A61B 2018/126* (2013.01); *A61B 2018/1467* (2013.01);
(Continued)

(58) Field of Classification Search
 CPC ......... A61B 18/10; A61B 18/12; A61B 18/14; A61B 18/1442; A61B 18/1445; A61B 18/1448; A61B 18/1482; A61B 2018/126; A61B 2018/1467; A61B 2218/002; A61B 2218/007; A61B 2218/008
(Continued)

(56) References Cited

U.S. PATENT DOCUMENTS 3,828,780 A    8/1974  Morrison, Jr.
5,084,045 A    1/1992  Helenowski
(Continued)

FOREIGN PATENT DOCUMENTS

DE    4138115 A1    5/1993
DE    4439553 C1    4/1996
(Continued)

OTHER PUBLICATIONS

European Search Report; Application No. EP 10 00 6191; dated Sep. 9, 2010; 6 pages.
(Continued)

*Primary Examiner* — Michael F Peffley
*Assistant Examiner* — Khadijeh A Vahdat
(74) *Attorney, Agent, or Firm* — Whitmyer IP Group LLC (57) ABSTRACT

A medical coagulation instrument having a shaft as well as at least one electrode tip that extends beyond the distal end of the shaft. To create a coagulation instrument whose electrodes are of simple structure and ensure an atraumatic and safe handling, at least one electrode tip should be widened or be configured as widening in the distal direction.

24 Claims, 6 Drawing Sheets (52) U.S. Cl.
CPC ... *A61B 2218/002* (2013.01); *A61B 2218/007* (2013.01); *A61B 2218/008* (2013.01)

(58) Field of Classification Search
USPC ..................................................... 606/41–50
See application file for complete search history.

(56) References Cited

U.S. PATENT DOCUMENTS

| | | | |
|---|---|---|---|
| 5,718,701 | A | 2/1998 | Shai et al. |
| 5,738,648 | A | 4/1998 | Lands et al. |
| 5,814,044 | A | 9/1998 | Hooven |
| 5,989,249 | A | 11/1999 | Kirwan, Jr. |
| 6,406,476 | B1 | 6/2002 | Kirwan, Jr. et al. |
| 2001/0020167 | A1 | 9/2001 | Woloszko et al. |
| 2002/0103485 | A1 | 8/2002 | Melnyk et al. |
| 2002/0111623 | A1 | 8/2002 | Durgin et al. |
| 2002/0133148 | A1* | 9/2002 | Daniel ............... A61B 18/1477 606/34 |
| 2003/0097126 | A1 | 5/2003 | Woloszko et al. |
| 2005/0015085 | A1 | 1/2005 | McClurken et al. |
| 2005/0119650 | A1 | 6/2005 | Sanders et al. |
| 2008/0086121 | A1 | 4/2008 | Sensenbrenner et al. |

FOREIGN PATENT DOCUMENTS

| | | |
|---|---|---|
| DE | 19541566 A1 | 5/1997 |
| DE | 20117907 U1 | 1/2002 |
| DE | 102005013871 A1 | 10/2005 |
| DE | 102004033595 A1 | 2/2006 |
| DE | 102005042312 A1 | 3/2006 |
| DE | 69635311 T2 | 4/2007 |
| GB | 2406057 A | 3/2005 |
| WO | 93098339 A1 | 5/1993 |
| WO | 0051510 A1 | 9/2000 |
| WO | 2005039427 A1 | 5/2005 |
| WO | 2006092563 A1 | 9/2006 |
| WO | 2006102124 A2 | 9/2006 |

OTHER PUBLICATIONS

International Preliminary Report on Patentability and Written Opinion of the International Searching Authority (translation); PCT/EP2009/000344; dated Sep. 7, 2010; 8 pages.

International Search Report and Written Opinion of the International Searching Authority; PCT/EP2009/000344; dated Apr. 8, 2009; 9 pages.

* cited by examiner

MEDICAL COAGULATION INSTRUMENT

FIELD OF THE INVENTION

The invention relates to a medical coagulation instrument having a shaft as well as at least one electrode tip extending beyond the distal end of the shaft.

BACKGROUND OF THE INVENTION

Medical coagulation instruments of this type are used in particular to close vessels during operations by means of the at least one electrode tip impinged with current.

Among medical coagulation instruments it is necessary to distinguish between so-called monopolar coagulation instruments and bipolar coagulation instruments. In so-called monopolar coagulation the coagulation instrument comprises an electrode tip that is impinged with current and by means of which the current, with heat generated, enters the tissue on the small contact surface of the electrode tip with the patient. The current is diverted by a neutral electrode with which the patient is in contact on a large surface. The large-surface contact of the patient with the neutral electrode prevents heat development at the current exit point.

In bipolar coagulation the coagulation instrument comprises two electrode tips that are electrically insulated from one another and which both are impinged with current so that energy, with local heat development, passes directly from one electrode tip to the other electrode tip.

A generic medical coagulation instrument configured as a bipolar coagulation instrument is known, for instance, from U.S. Pat. No. 2008/0086121 A1.

A disadvantage of coagulation instruments known in the art is that injuries to patients can result from the insertion of the instrument into the operating area through the at least one electrode extending beyond the distal end of the instrument shaft. In addition, this at least one electrode tip presents only a small distal coagulation surface and is unstable because of its structural configuration.

Consequently it is the object of the invention to configure a bipolar coagulation instrument of the aforementioned type in such a way that its electrodes ensure both simple construction and atraumatic and safe handling.

It is yet another object of the invention to provide a coagulation instrument that allows electrodes to be affixed to the shaft of the coagulation instrument more easily and/or securely during manufacture.

SUMMARY OF THE INVENTION

This object is achieved in such a way, according to the invention, that the at least one electrode tip is configured as widening in a distal direction. This widening can be either constant or in stages in the axial direction of the coagulation instrument pointing distally. With a step-wise widening, however, attention is required to ensure that said widening is achieved in a position and manner that are atraumatic when applied in an operation.

As a result of the inventive configuration of the electrode tips as widening in the distal direction, it is possible to increase the stability and solidity of the electrodes and simultaneously to reduce the risk of injury to the patient because of the distal widening of the electrodes.

In configuring the medical coagulation instrument as a bipolar coagulation instrument, it is proposed with the invention that two electrode tips that extend beyond the distal end of the shaft and are electrically insulated against one another should be positioned on the distal end of the shaft and should both be configured as widening in the distal direction.

According to a practical embodiment of the invention it is proposed that the electrodes should be configured as thickening in the distal direction in order to increase the solidity of the electrodes by the more massive configuration of the electrode tips.

According to one embodiment of the invention it is proposed that the electrodes should be configured as widening conically in the distal direction. Conical configuration of the electrode tips constitutes an embodiment of the electrodes that is especially easy to manufacture and safe to handle, and which combines increased solidity and simultaneous operational safety.

According to an alternative embodiment of the invention it is proposed that the electrodes should be configured as widening in fan-like manner in the distal direction. Fan-shaped widening of the electrode tips can also lead to increased intrinsic solidity of the electrode tips along with reduction of the risk of injury.

It is further proposed with the invention that to improve the atraumatic operation of the coagulation instrument, the free ends of the electrodes should be configured as rounded.

In addition it is proposed with a preferred embodiment of the invention that to simplify production of the coagulation instrument, a small plate should be applied on the outside on an electrode tip, and in particular it should be welded in place. In this manner the invention includes all manners of joining the small plates to the respective electrode tip and also all combinations of various ways of joining the two small plates.

This small plate preferably and in particular should have the width of the electrode tip so that the entire structure of the electrode tip and the small plate applied to it should form almost a thickened electrode tip.

The distal end of the small plate here can extend as far as the distal end surface of the electrode or of the electrode tip.

The small plate is in particular a pipe segment, but more particularly in the shape and curvature of the electrode tip.

The small plate can have the thickness of the electrode tip or else a lesser or greater thickness.

According to the invention the thickness of the small plate can be constant. However, the thickness of the small plate can also change in the axial direction of the coagulation instrument, in particular widening in the distal direction, or else it can in particular be conical. Besides conical form, the change in thickness of the small plate can also take any other form, such as convex or concave, constant or non-constant.

In the same manner the thickness can also change during the tangential course of the electrode tip. For instance, the thickness can decrease in the direction toward the tangential external portions of the small plate.

To reduce still further the risk of injury from the tangential outer portions of the electrode tip, the small plate could also be widened on its tangential outer portions.

Like the thickness of the electrode tips, the thickness of the small plate can also vary according to the invention. For instance, the thickness of the small plate can increase conically over its axial course, in particular in the distal direction.

The thickness of the small plate can also vary over the tangential course of the small plate. For instance, the thickness in the direction toward the tangential outside portions of the small plate can decrease or else can increase.

In an additional embodiment a small plate can be affixed on the inside of the electrode tip, and in particular can be welded to the electrode tip, in addition to or instead of the small plate on the outside of the electrode tip at the distal end portion of the free end of the electrode.

This inside small plate preferably has the shape and width of the electrode tip.

The inside small plate here is, in particular, a pipe segment.

The inside small plate here can have the thickness of the electrode tip or else a lesser or greater thickness.

According to the invention the thickness of the inside small plate can also vary. For example, the thickness of the inside small plate can increase conically along its axial course, in particular in the distal direction.

The thickness of the inside small plate can also vary along the tangential course of the small plate. For example, the thickness can decrease in the direction toward the tangential outer portions of the inside small plate.

The outer and/or inside small plate can be affixed not just to one of the two electrodes, but also to both, and in particular can be welded in any form, thus for instance the inside small plate on one electrode and the outside small plate on the other, the inside or outside small plate on both electrodes, or only the inside or outside small plate on one electrode and both small plates on the other. The respective small plates here can each independently have any of the described thickness or thickness changes.

In other aspects a medical coagulation instrument is provided and includes a shaft and a conductive section of the shaft extending along an axis of the shaft. An electrode has a base section and an end section extending out a distal end of the shaft from the base section, the base section having a same cross section as the conductive section of the shaft. A distal end of the conductive section joined to a proximal end of the base section such that an axis of the base section aligns with the axis of the shaft.

A width of the end section may increase in a distal direction such that the width is measured between inner and outer surfaces of the end. An insulating section may be disposed around an outer surface of the conductive section and extending beyond the distal end. An outer surface of the electrode may align with an outer surface of the insulating section. The electrode may further include a first section of the end of a first thickness equal to a wall thickness of the conductive section. A second section of the end may be located distally of the first section of the end, the second section of the end may have a second thickness greater than the first thickness. The second section of the end may include a small plate affixed thereto. The distal end of the conductive section may be joined to the proximal end of the base section by welding. A second conductive section may be disposed around the first conductive section such that an inner surface of the second conductive section is spaced apart from an outer surface of the conductive section. A second electrode may have a base section with an inner surface, the inner surface spaced apart from an outer surface of the base section of the electrode such that the base section of the second electrode is located around the base section of the electrode. An insulating section may be located between the conductive section and the second conductive section. The insulating section may extend beyond the distal end of the conductive section and between the bases of the electrode and the second electrode.

In other aspects a medical coagulation instrument includes a shaft having two tubular conductive sections extending along an axial direction of the shaft. A first one of the two tubular conductive sections circumscribes a second one of the two tubular conductive sections, the first one and the second one of the two tubular conductive sections is electrically insulated with respect to each other. A first electrode may have a first base, the first base may be tubular and connected to a distal end of the first one of the two tubular conductive sections. A second electrode may have a second base, the second base may be disposed around the first base such that the first and second bases are coaxial, the second base may be connected to a distal end of the second one of the two conductive sections.

A third section of the shaft may be made of an electrically insulating material and disposed between the two tubular conductive sections. An end section may extend out a distal end of the shaft from the base section wherein an end section of at least one of the two electrodes has a width increasing in a distal direction. A first inner surface and a first outer surface of the end section may correspond to the first electrode, a second inner surface of the end section may correspond to the second electrode. The width of each of the first and second electrode sections may be measured between the inner and outer surfaces corresponding to the first and second electrode sections.

The first and second ones of the two conductive sections may be configured as a cylinder, the first and second bases may further be configured as a cylinder. An insulating member may be disposed around the second one of the two conductive sections. A first and second joint may be located respectively at the first and second bases where the first and second bases respectively connect to the first and second ones of the two conducting sections. The insulating member may extend in a distal direction beyond at least one of the first and second joints.

A first and second joint may be located respectively at the first and second bases where the first and second bases respectively connect to the first and second ones of the two conducting sections. The first and second joints may be formed by welding.

In other aspects a medical coagulation instrument is provided with a shaft having a distal end. Two electrode tips may extend beyond the distal end, the two electrode tips electrically insulated with respect to each other. A width measured between an inner and an outer surface of at least one of the two electrode tips may increase in a distal direction. The shaft may be hollow to define a channel extending along an axis of the shaft and between the two electrode tips.

The two electrode tips may be oriented such that an inner surface of each of the two electrode tips faces towards each other and an outer surface of each of the two electrode tips faces away from one another, at least one of the two electrode tips may have a second curved cross section and a second curved surface. At least one of the two electrode tips may have a curved cross section such that at least one of the inner or outer surfaces is curved. The small plate may be joined to the at least one of the two electrode tips, the small plate having a curved cross section such that a surface of the small plate contacts one of the inner or outer surfaces. The two electrode tips may be configured as thickening in the distal direction. The two electrode tips may widen conically in the distal direction. The distal end of at least one of the two electrode tips may be configured as rounded.

The shaft may include first and second conductive sections, the second conductive section arranged around the first conductive section such that an inner surface of the second conductive section is spaced apart from an outer surface of the first conductive section. A first one of the two electrode tips may be connected to a first base. A second one of the two electrode tips may be connected to a second base.

A proximal end of the first base may be connected to a distal end of the first conductive section and a proximal end of the second base may be connected to a distal end of the second conductive section. The first and second bases may be respectively connected to the first and second conductive sections by welding. An insulting section may be disposed between the first and second conductive sections. The insulating section may extend between the first and second bases.

A small plate may be affixed to at least one of the two electrode tips to form a thickened surface at a distal end of at least one of the two electrode tips by joining of the at least one small plate to the at least one of the two electrode tips such that a distal edge of the at least one small plate and a distal edge of the at least one of the two electrode tips align.

A small plate may be affixed to at least one of the two electrode tips, the small plate having a distal surface. The distal surface of the small plate and a distal surface of the at least one of said two electrode tips may be aligned and located in a common plane.

Additional properties and advantages of the invention can be seen from the appended illustrations, in which an embodiment of an inventive medical coagulation instrument is presented by way of example, without restricting the invention to this embodiment.

DETAILED DESCRIPTION OF THE INVENTION

Figures 1, 2:
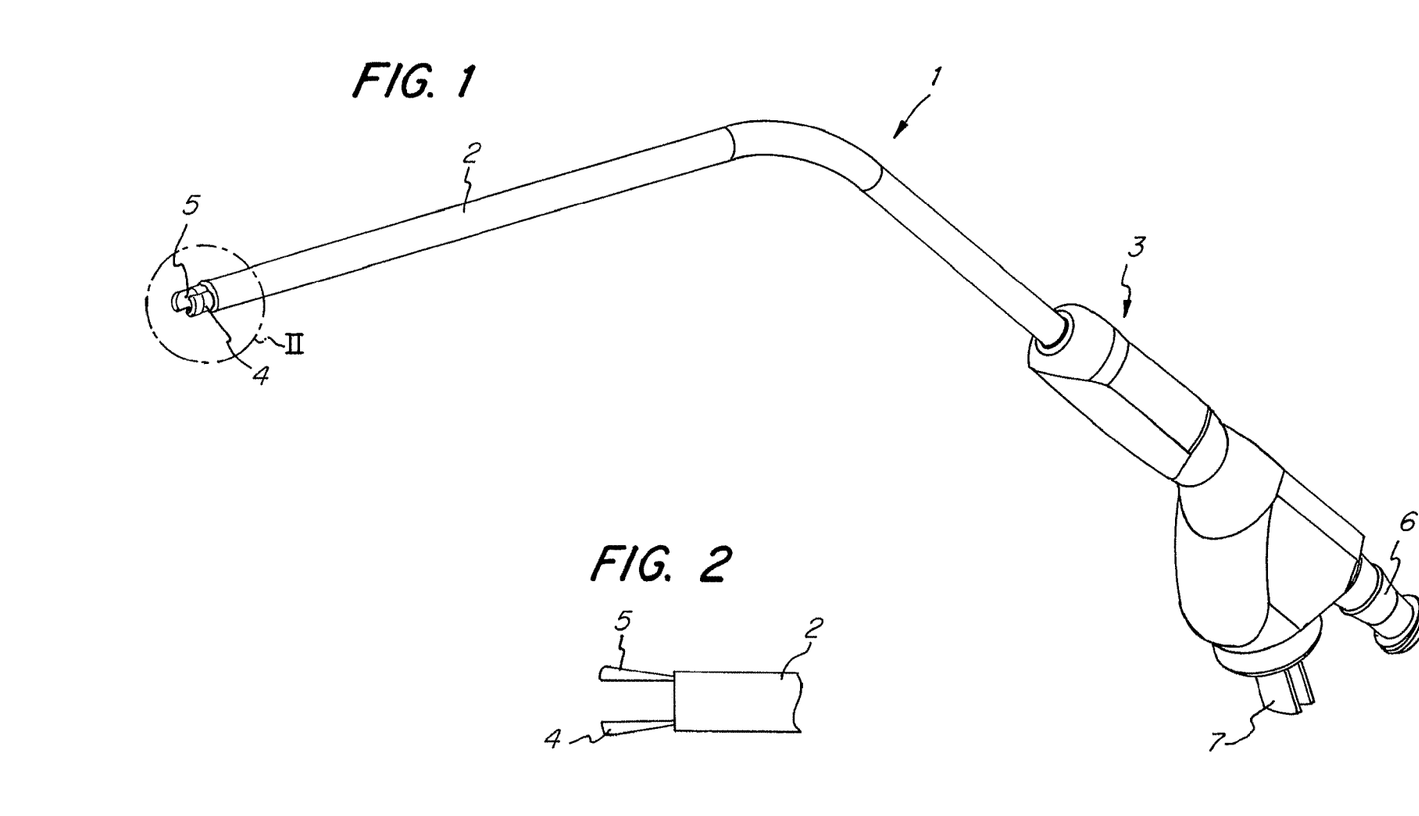
FIG. 1 presents a perspective side view of an inventive medical coagulation instrument.
FIG. 2 presents an enlarged depiction of detail II according to FIG. 1 in overhead view.

FIG. 1 shows a medical coagulation instrument 1 that is configured as a bipolar coagulation instrument 1 and is also configured as a suction instrument in addition to its configuration as a coagulation instrument.

This illustrated medical bipolar coagulation instrument 1 consists essentially of a hollow shaft 2 configured as a suction/irrigation channel, a handle 3 positioned on the proximal end of the shaft 2, and two electrode tips 4 and 5 that extend beyond the hollow shaft 2 on the distal end.

To configure the hollow shaft 2 as a suction and/or irrigation channel, the handle 3 comprises on its proximal end a suction and/or irrigation connection 6 for coupling with an external suction and/or irrigation line. The electrode tips 4 and 5 are impinged by means of a current connection 7 positioned on the handle 3.

As can be seen in particular from the detail view of FIG. 2, the finger-type protruding electrode tips 4 and 5 are positioned opposite to one another and are electrically insulated from one another on the distal end of the shaft 2 in such a way that they extend beyond the distal end of the shaft 2.

To give the electrode tips 4 and 5 a higher degree of solidity, the electrode tips 4 and 5 are configured to widen in the distal direction. In the presented embodiment the electrode tips 4 and 5 are configured as widening conically in the distal direction in such a way that the electrode tips 4 and 5 are clearly configured as thicker on the free distal end than at the proximal transition to the shaft 2.

Alternatively to the illustrated conical widening of the electrode tips 4 and 5 toward the distal end, it is also possible to achieve this distal-end widening of the electrode tips 4 and 5 by a fan-shaped widening of the free distal ends of the electrode tips 4 and 5.

In addition to the increase in solidity of the electrode tips 4 and 5, the widening of the free distal ends of the electrode tips 4 and 5 causes an enlargement of the coagulation surfaces, that is, of the surfaces by which the current by heat development enters the patient's tissue.

An additional decisive advantage of the widening of the distal-end free ends of the electrode tips 4 and 5 consists in the fact that the risk of injury to the patient during insertion of the coagulation instrument 1 into the operating area is clearly reduced if the free ends of the electrode tips 4 and 5 are no longer thin and narrow but rather widened and thickened in configuration.

To further improve the possibility of atraumatic use of the coagulation instruments 1 by the widening outward of the electrode tips 4 and 5, the free ends of the electrode tips 4 and 5 shown in FIG. 2 have in addition a rounded-off configuration.

Figure 3:
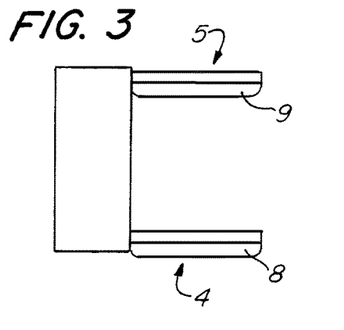
FIG. 3 presents an enlarged depiction of detail II according to FIG. 1 of a preferred embodiment of the invention in overhead view.

FIG. 3 shows a preferred embodiment of the invention in enlarged view, that is, corresponding to detail II of FIG. 1 in overhead view.

Here the electrode tips 4 and 5 widen in the distal direction, to some extent in stages. In this arrangement, the small plates 8, 9 are affixed to the electrode tips 4 and 5, in particular by welding. All means of joining and combining the small plates 8 and 9 to the respective electrode tips 4 or 5 are also possible.

In this preferred embodiment a small plate 8 is affixed on the outside of electrode tip 4. The small plate 8 can have a constant thickness as shown here.

It is also possible, alternatively, for the thickness of the small plate 8 to change in the axial direction of the coagulation instrument 1, in particular by widening in the distal direction, in particular conically. The thickness of the small plate 8 can likewise be reduced in the distal direction, in particular conically. Aside from conically, the change in thickness of the small plate 8 can also be configured in any other manner, for instance as convex or concave, constant or non-constant. It is particularly preferred for the small plate 8 to be reduced on its edges, in particular the distal edges, in particular by rounding.

This small plate 8 preferably has the shape and in particular the width of the electrode tip 4, so that the total structure of the electrode tip 4 with the small plate 8 affixed to it should form a thickened electrode tip 4. It is important here that the small plate 8 should extend essentially as far as the distal end surface of the electrode or of the electrode tip 4.

Although it is illustrated only in section in FIG. 3, the small plate is preferably a pipe segment, but in particular with the shape and curvature of the electrode tip 4.

As shown in FIG. 3, a small plate 9 is affixed to the electrode tip 5. The small plate 9, like small plate 8, can have a constant thickness. Alternatively, the small plate 9 could have a variable thickness as described for small plate 8. Here all combinations of variable thickness are possible for the small plates 8 and 9.

The shape and in particular the width of the small plate 9 can be the same as for small plate 8, such that all combinations of these various types of shape or of width are possible for the small plates 8 and 9.

Figure 4:
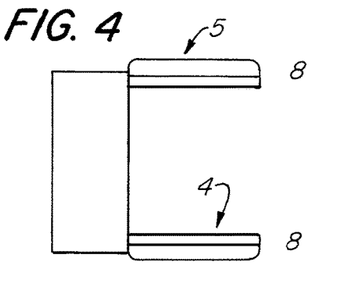
FIG. 4 presents an enlarged depiction of detail II according to FIG. 1 of a second preferred embodiment of the invention in overhead view.

FIG. 4 shows a second preferred embodiment of the invention in enlarged view, that is, corresponding to detail II of FIG. 1 in overhead view.

As in FIG. 3, the electrode tips 4 and 5 widen here in the distal direction, to some extent in stages. Here the small plates 8 are affixed to the electrode tips 4 and 5, in particular by welding. It is also possible to use any manner of joining and combining the small plates 8 to the respective electrode tip 4 or 5.

In this second preferred embodiment, a small plate 8 is affixed on the outside on the electrode tip 4. The small plate 8 can have a constant thickness, as described here.

Alternatively, however, the thickness of small plate 8 could also vary in the axial direction of the coagulation instrument 1, in particular widening in the distal direction, in particular conically. The thickness of the small plate 8 can likewise decrease in the distal direction, in particular conically. Aside from conical shape, the variation in thickness of the small plate 8 can also be achieved in any other manner, for instance convex or concave, constant or non-constant. It is especially preferred that the small plate should be reduced on its edges, in particular the distal edge, and in particular by rounding.

This small plate 8 preferably has the shape and in particular the width of the electrode tip 4, so that the total structure of the electrode tip 4 with its applied small plate 8 forms a thickened electrode tip 4. It is important here that the small plate 8 should extend essentially as far as the distal end surface of the electrode and/or of the electrode tip 4.

Although shown only in section in FIG. 4, the small plate is preferably a pipe segment, but in particular with the shape and curvature of the electrode tip 4.

A small plate 8 is likewise affixed externally on the electrode tip 5 according to FIG. 4.

This small plate 8 can have a constant thickness or else, as described for small plate 8, can comprise on the electrode tip 4 a variable thickness. Here all combinations of varying thickness are possible for both small plates 8.

The shape and in particular the width of this small plate 8 can be as described for the small plate 8 on the electrode tip 4, so that all combinations of these various types of shape and/or of width are possible for both small plates 8.

Figure 5:
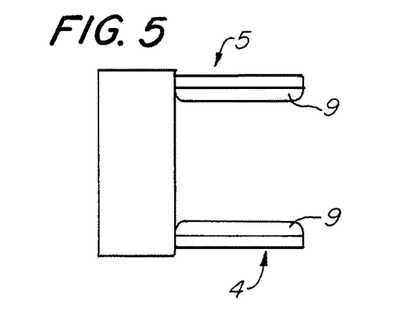
FIG. 5 presents an enlarged depiction of detail II according to FIG. 1 of a third preferred embodiment of the invention in overhead view.

FIG. 5 presents a third preferred embodiment of the invention in enlarged view, that is, corresponding to detail II of FIG. 1 in overhead view.

As in FIGS. 3 and 4, here the electrode tips 4 and 5 widen in the distal direction, to some extent in stages. In addition, small plates 9 are affixed to the electrode tips 4 and 5, in particular by welding. All means of joining and combining the small plates 9 to the respective electrode tip 4 or 5 can be considered.

With this third preferred embodiment, a small plate 9 is affixed to the electrode tip 4 on the inside. As shown here, the small plate 9 can have a constant thickness.

Alternatively, the thickness of the small plate 9 could also vary in the axial direction of the coagulation instrument 1, or in particular could widen in the distal direction, in particular conically. Likewise the thickness of the small plate 9 can also decrease distally, in particular conically. In addition to conical variation, the thickness of the small plate 9 can also take any other form, for instance convex or concave, constant or non-constant. It is especially preferable that the small plate 9 should be reduced on its edges, in particular the distal edge, in particular by rounding.

This small plate 9 preferably has the shape and in particular the width of the electrode tip 4, so that the entire structure of the electrode tip 4 with its affixed small plate 9 should form a thickened electrode tip 4. It is important here that the small plate 9 should extend essentially as far as the distal end surface of the electrode or of the electrode tip 4.

Although shown only in section in FIG. 5, the small plate is preferable a pipe segment, but in particular with the shape and curvature of the electrode tip 4.

A small plate 9 is likewise affixed on the inside to the electrode tip 5 as in FIG. 5.

This small plate 9 can have a constant thickness or else, as described for small plate 9 on the electrode tip 4, can have a variable thickness. Here all combinations of varying thickness are possible for both small plates 9.

The shape and in particular the width of this small plate 9 can be as described for small plate 9 on the electrode tip 4, such that all combinations of these various types of shape or of width are possible for both small plates 9.

Figure 6:
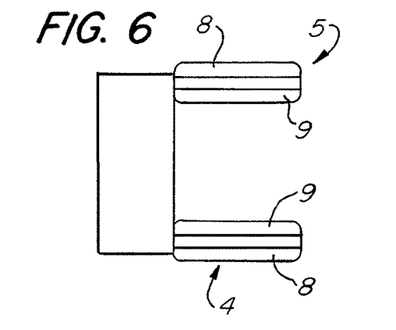
FIG. 6 presents an enlarged depiction of detail II according to FIG. 1 of a fourth preferred embodiment of the invention in overhead view.

FIG. 6 shows a fourth preferred embodiment of the invention in enlarged view, that is, corresponding to detail II of FIG. 1 in overhead view.

Here, as in FIGS. 3 and 4, the electrode tips 4 and 5 widen in the distal direction and to some extent in stages. Thus small plates 8 and 9 are affixed onto the electrode tips 4 and 5, respectively, in particular by welding. It is also possible to use any types or combinations in joining the small plates 8 and 9 onto the respective electrode tip 4 or 5.

In this fourth preferred embodiment a small plate 8 on the inside and a small plate 9 on the outside are affixed to the electrode tip 4. The small plate 8 like small plate 9 can have a constant thickness as shown here.

The thickness of the plate 8 or 9 could vary alternatively but in each case also in the axial direction of the coagulation instrument 1, in particular widening in the distal direction, in particular conically. The thickness of the small plate 8 or 9 can likewise decrease in the distal direction, in particular conically. Besides changing conically, the change in thickness of the small plate 8 or 9 can be of any other type, for example convex or concave, constant or non-constant. It is especially preferred that the small plates 8 or 9 should be reduced on their edges, particularly on the distal edge, in particular by rounding. Thus the thickness and reduction/rounding of both small plates 8 and 9 can operate differently and/or for one of the two small plates 8 and 9 the thickness could change and for the other it could not, so that all corresponding combinations are conceivable.

The small plate 8 or the small plate 9 preferably have the shape and in particular the width of the electrode tip 4, so that the entire structure of the electrode tip 4 with its affixed small plates 8 and 9 forms a thickened electrode tip 4. It is important here that the small plate 8 and the small plate 9 extend essentially as far as the distal end surface of the electrode or of the electrode tip 4.

Although shown only in section in FIG. 6, the small plates 8 and 9 are preferably pipe segments, but in particular of the shape and curvature of the electrode tip 4.

According to FIG. 6 a small plate 8 is affixed on the electrode tip 5 on the outside and a small plate 9 on the outside.

These small plates 8 or 9 can each have a constant thickness or else a varying thickness as described for the small plates 8 or 9 on the electrode tip 4. All combinations of varying thickness are possible here for the two small plates 8 or 9.

The shape and in particular the width of these small plates 8 or 9 can be as described for the small plates 8 or 9 on the electrode tip 4, such that all combinations of these various types of shape or width are possible for both small plates 8 or 9.

The medical coagulation instrument configured according to the invention or to the described embodiments is distinguished in that, on the basis of the distal widening of the free ends of the electrode tips 4 and 5, an atraumatic handling of the coagulation instrument is ensured along with simultaneously clearly improved solidity of the electrode tips 4 and 5.

Alternatively to the depiction in FIGS. 1, 2, 3, 4, 5, and 6, it is also possible of course to employ this distal widening of the electrode tips 4 and 5 with other bipolar coagulation instruments or else with monopolar coagulation instruments equipped with only one electrode tip 4.

Figure 7:
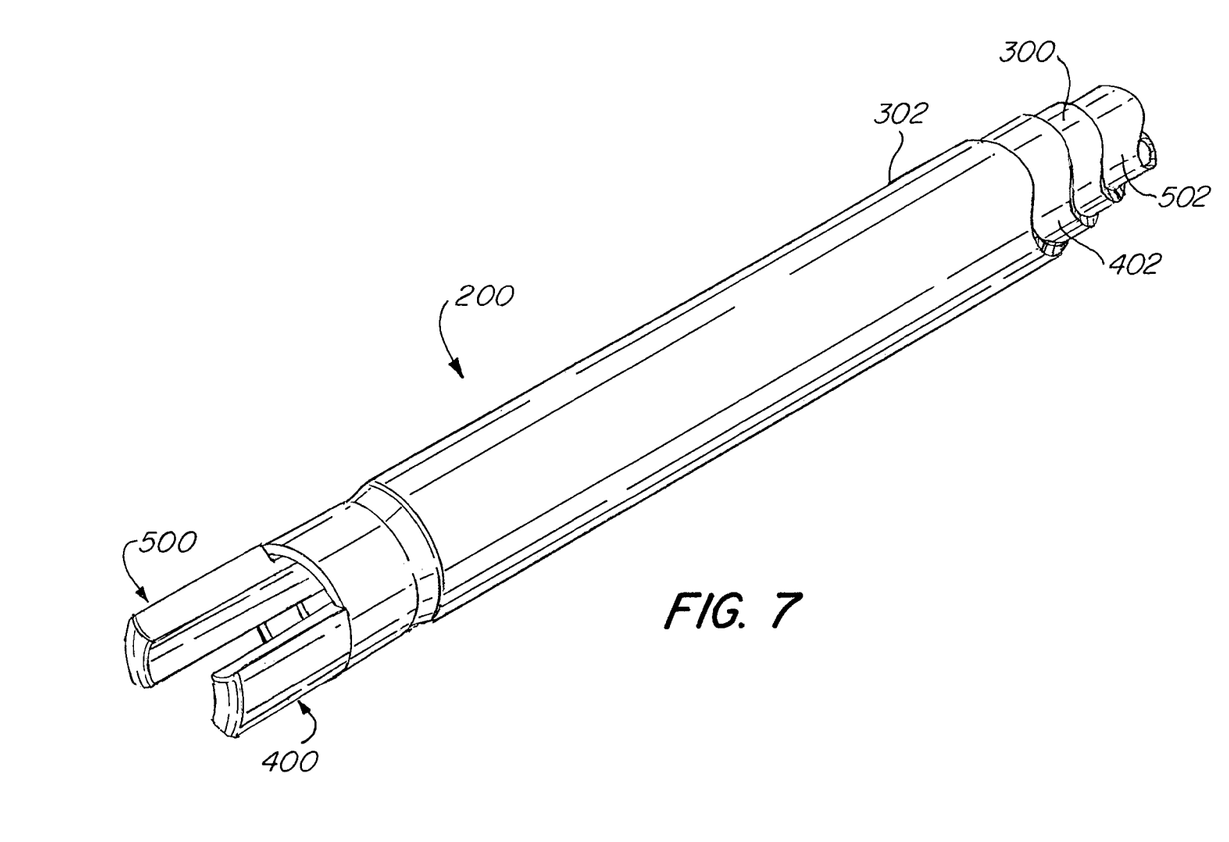
FIG. 7 is a perspective side view of part of a medical coagulation instrument having some features similar to the medical coagulation instrument shown in FIGS. 1-6.

In FIG. 7 electrodes 500 and 400 are shown extending from a shaft 200 of an instrument, these electrodes may be welded to the shaft, for example by laser welding. Instrument is similar to coagulation instrument 1. As an example the proximal end of the instrument of FIG. 7 may be the same or similar to the one shown in FIG. 1.

Figure 8:
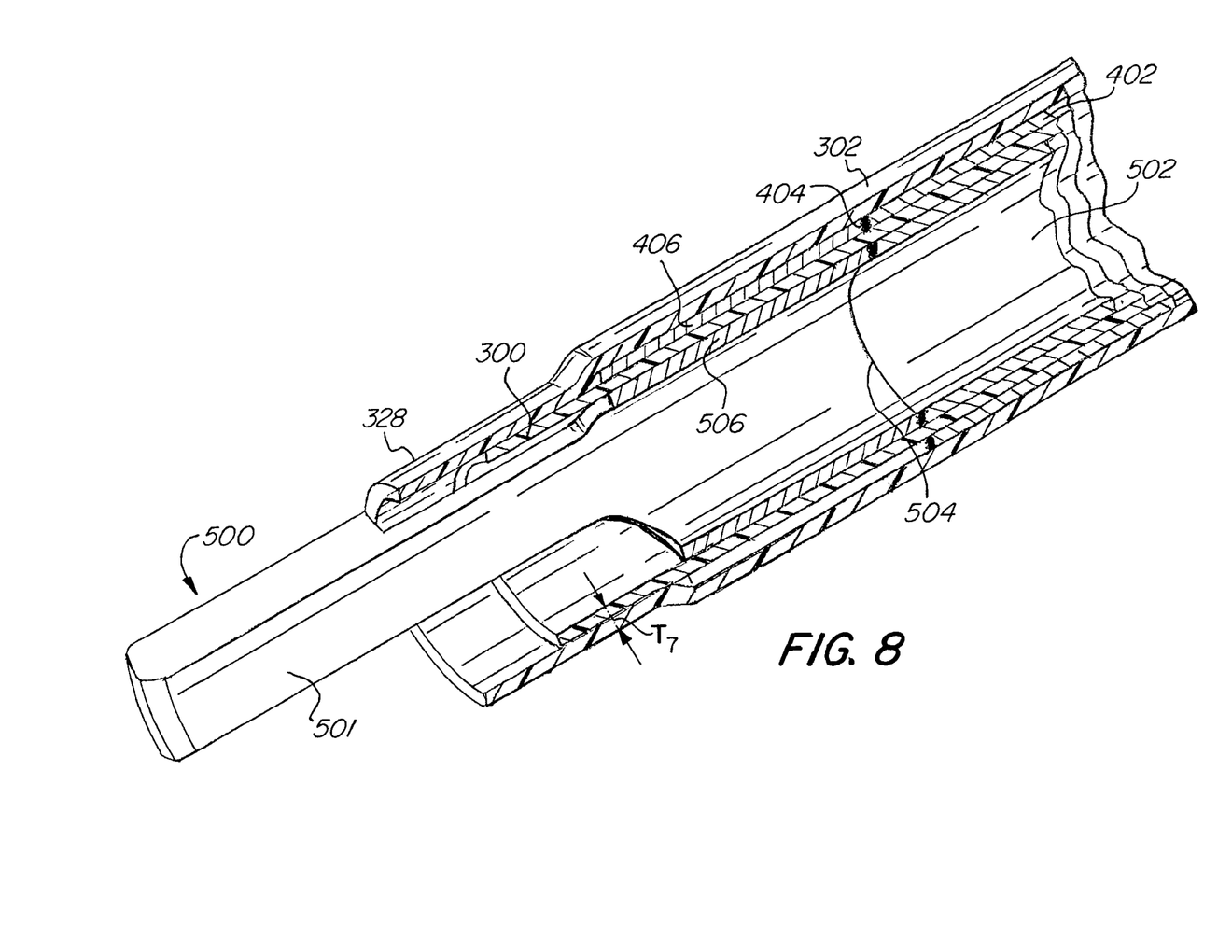
FIG. 8 is a first cross section view of the medical coagulation instrument of FIG. 7.

In FIG. 8 a cross section view shows the side of the instrument 100 with electrode 500. As can be seen electrode 500 is the inner electrode and attaches to a conductive section 502 which is shown as the inner one of two conductive sections. The joint 504 is located between a proximal end 512 of base 506 of the electrode 500 and the distal end 550 of the conductive section 502. Spaced apart from conductive section 502 is a conductive section 402 which is shown as the outer of the two conductive sections. Between conductive sections 502 and 402 is an insulating layer 300 which helps to keep the conductive sections 502 and 402 electrically insulated from each other.

Figure 9:
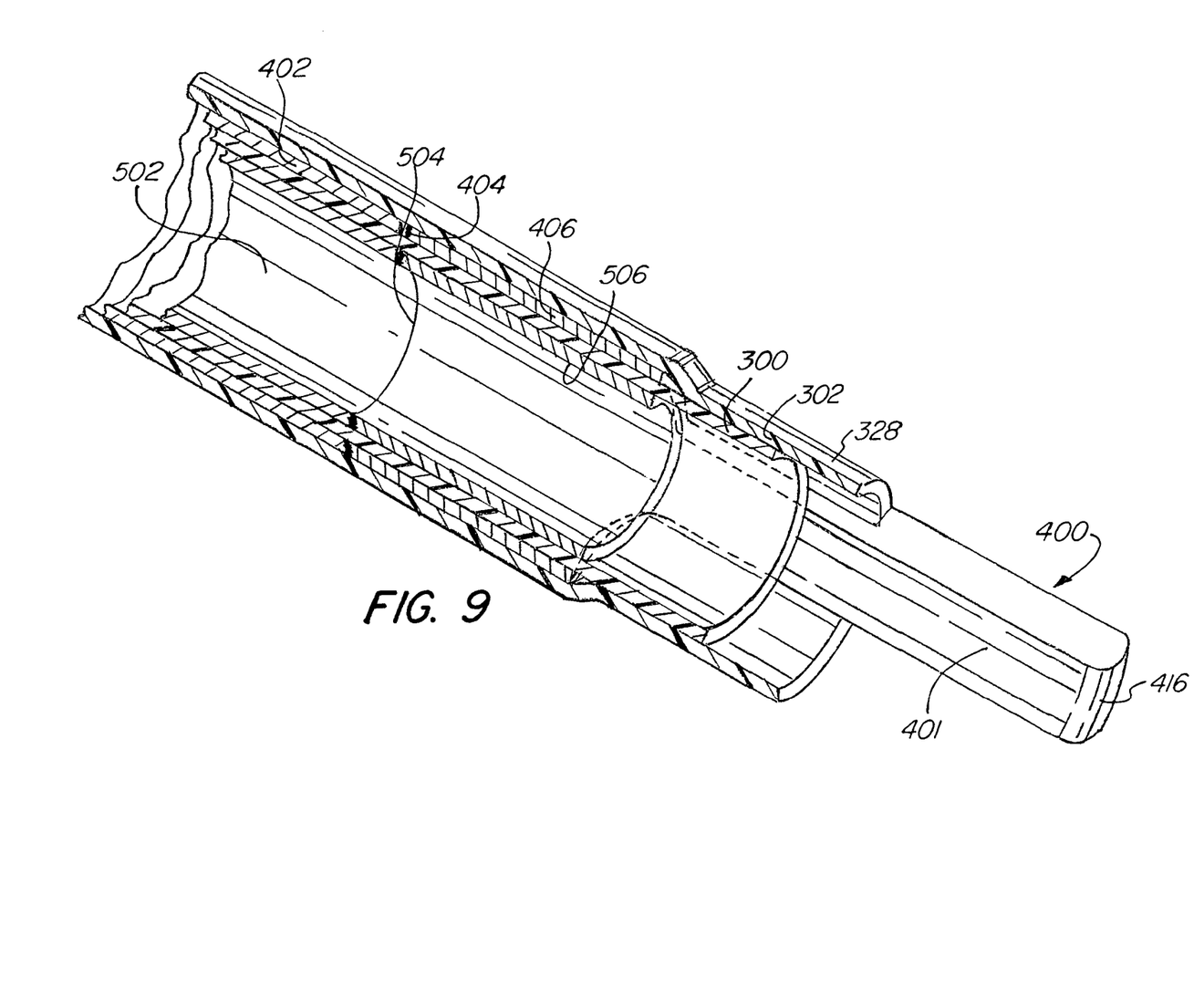
FIG. 9 is a second cross section view of the medical coagulation instrument of FIG. 7.

Referring to FIG. 9, the alternate side of the cross section of FIG. 8 is shown. Here, more detail can be seen with respect to the section 410 of the electrode which is located between insulating sections 300 and 302. The joint 404 is located between base 406 and conductive section 402 such that the distal end 450 of conductive section 402 is in contact with the proximal end of base 406. Joints 404 and 504 may be welded, for example by laser welding. The joints 404 and 504 shown are butt joints such that two flat surfaces are joined together. For example proximal end 512 of electrode 500 contacts distal end 550 of conductive section 502.

It is understood that other methods of joining may be used as would be understood by one of skill in the art. Further, the contact area of the joint may be of a shape other than a cylinder or tube. For example, square, rectangular, oval, eliptical and other shaped sections, tubes or parts thereof may be employed for bases 406/506 and conductive sections 402/502. Further, the joints 404/504 are shown in a plane perpendicular to the axis 102 of the shaft. It is understood that the joints 404/504 may be configured such that they are in one or more planes and/or located at an angle other than 90 degrees relative to the axis 102 of the shaft.

Figure 10:
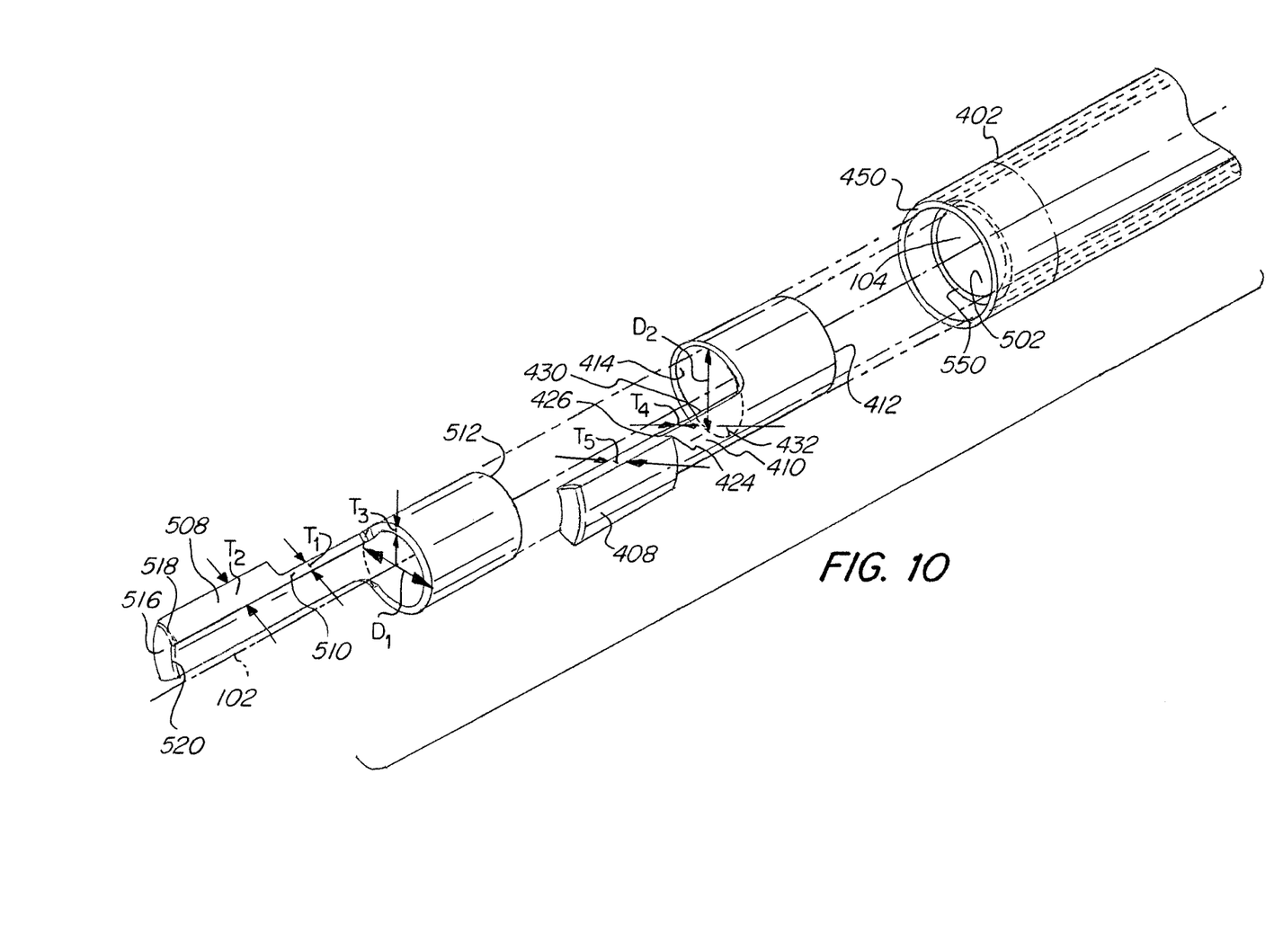
FIG. 10 is an exploded perspective view of the medical coagulation instrument of FIG. 7.

In FIG. 10 electrodes 500 and 400 are respectively shown. The end 401/501 of the electrode 400/500 may have two sections 408/508 and 410/510. Referring to electrode 500, section 510 has a thickness T1 smaller than thickness T2. Further, T1 may also be the same as the thickness T3 of the base 506. The base 506 is configured as a cylinder in the depicted embodiment with an outer diameter D1 it is understood that other cross sections for the base and conductive sections may be used.

Referring to electrode 400, section 410 may have a thickness T4 which in some cases may be equal to thickness T1. Base 406 has an inner diameter D2 which is larger than diameter D1 to allow insulating material 302 to be located between the bases to electrically insulate the electrodes with respect to each other. Section 408 has a thickness T5 which may be equal to thickness T2 in some cases. Since electrode 400 is the outer electrode, the end 408 may extend both outwards and inwards with respect to section 410. For example outer protrusion 424 and inner protrusion 426 may add to the overall thickness of the end 408. This allows the outer surface 428 of electrode 400 to align with the outer surface 328 of the outer section of the shaft. In addition, the difference between thickness T1 and T2 may be approximately equal to the combined thickness T7 of insulating sections 300/302. Since electrode 400 is the outer electrode, the outer surface of insulating section 300 would face inner surface 430 of section 410 of the electrode 400 and the inner surface of insulating section 302 would face the outer surface 432 of section 410 of the electrode. Thus, the protrusion 424 extends from the outer surface 432 at a distance approximately equal to the thickness of insulating section 302.

The inner diameter D2 of base 406 as shown is larger than D1 such that a space is created between the inner surface 414 of base 406 and the outer surface 514 of base 506. This allows space for the insulating material 300 to be located between the bases 406/506 and between the conductive sections 402/502.

When joined together, the electrodes 400/500 share a common axis 102 with conductive sections 402/502 such that base 406 is circumscribed around base 506 and conductive section 402 is likewise circumscribed around conductive section 502.

The space 104 may be configured as a suction/irrigation channel similar to the channel described with respect to FIGS. 1-6. Although sections 408/508 are shown as made of a continuous material, it is understood that the small plate shown and described herein with respect to FIGS. 1-6 may be affixed to the end 501 of the electrode to provide for increasing thickness/width of the electrode at the distal end and to provide a larger distal coagulation surface 516 than if no plate were present. The distal end of the electrode 500 is also shown with rounded edges 518/520 which may provide for atraumatic handling of the coagulation instrument during operations.

Although bases 406/506 are shown a cylindrical tube sections, it is understood that other tube sections may be used. For example, square, rectangular, elliptical and other cross sections are contemplated. In addition, the base may not be configured as a completely closed cross section, but a section that matches the corresponding conductive section.

The ends of the electrodes 400/500 are shown with the vertical edges (ie those perpendicular to the axis) configured as rounded. The horizontal edges of the electrode may also be configured as rounded, which may increase the safe handling of the electrode.

The increasing width of the electrode at the end may provide for reduced current density at the ends of the electrode in comparison to an electrode that does not widen in the distal direction.

Although the figures shown herein generally show a bipolar coagulation instrument, it is understood that the devices may be modified to include a single electrode. It is also understood that although the conductive sections/electrodes are electrically insulated with respect to each other, the device(s) shown herein may be configured to act as a monopolar coagulation instruments with two electrode tips of a common polarity. In this configuration, the polarity of both conductive sections/electrodes may be the same and a grounding pad or opposite polarity electrode is affixed or in contact separately with the body being operated on.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A medical coagulation instrument comprising:
   a shaft;
   a conductive section of said shaft, said conductive section of said shaft extending along a length of said shaft;
   an electrode having a base section and an end section extending in a distal direction out a distal end of the base section, the base section having a same cross section as said conductive section of said shaft;
   the electrode being one piece;
   a distal end of said conductive section of said shaft being joined to a proximal end of the base section such that a central longitudinal axis of said base section aligns with a central longitudinal axis of said shaft;
   the end section having an inner surface facing the central longitudinal axis of the base section and having an outer surface facing opposite the inner surface;
   said end section having a width, the width increasing in the distal direction and being measured between the inner surface and the outer surface of said end section.

2. The medical coagulation instrument of claim 1 further comprising:
   an insulating section disposed around an outer surface of said conductive section of said shaft and extending beyond said distal end of said conductive section of said shaft.

3. The medical coagulation instrument of claim 2 further comprising:
   an outer surface of said electrode aligning with an outer surface of said insulating section.

4. The medical coagulation instrument of claim 1 wherein said electrode further comprises:
   a first section of said end section of a first thickness equal to a wall thickness of said conductive section of said shaft;
   a second section of said end section located distally of said first section of said end section, said second section of said end section having a second thickness greater than the first thickness.

5. The medical coagulation instrument of claim 1 wherein the distal end of said conductive section of said shaft is joined to the proximal end of the base section by welding.

6. The medical coagulation instrument of claim 1 wherein said conductive section of said shaft is a first conductive section, and said shaft comprises a second conductive section disposed around said first conductive section of said shaft such that an inner surface of said second conductive section is spaced apart from an outer surface of said first conductive section of said shaft;
   wherein said electrode is a first electrode;
   said medical coagulation instrument further comprises a second electrode having a base section with an inner surface, the inner surface of the second electrode spaced apart from an outer surface of the base section of said first electrode such that the base section of said second electrode is located around the base section of said first electrode.

7. The medical coagulation instrument of claim 6 further comprising:
   an insulating section disposed between said first conductive section of said shaft and said second conductive section of said shaft.

8. The medical coagulation instrument of claim 7 wherein said insulating section extends beyond said distal end of said conductive section of said shaft and between the bases of said first electrode and said second electrode.

9. A medical coagulation instrument comprising:
   a shaft having two tubular conductive sections extending along a length of said shaft;
   a first one of said two tubular conductive sections circumscribing a second one of said two tubular conductive sections, said first one and said second one of said two tubular conductive sections electrically insulated with respect to each other;
   a first electrode having a first base, the first base is tubular and has a proximal end, the proximal end of the first base is connected to a distal end of said first one of said two tubular conductive sections;
   a second electrode having a second base, the second base disposed around the first base such that said first and second bases are coaxial, the second base has a proximal end, the proximal end of the second base is connected to a distal end of said second one of said two tubular conductive sections;
   the first electrode and the second electrode each being a single piece;
   a first end section extending out a distal end of the first base and a second end section extending out a distal end of the second base;
   the first end section and the second end section each having an inner surface and an outer surface, the inner surface facing a central longitudinal axis of the shaft, and the outer surfaces facing opposite the inner surfaces;
   the end section of at least one of the first electrode of the second electrode having a width increasing in a distal direction, the width measured between the inner and the outer surface of the end section of the at least one of the first electrode or the second electrode.

10. The device of claim 9 further comprising:
    a third section of said shaft made of an electrically insulating material and disposed between said two tubular conductive sections.

11. The device of claim 9 wherein said first one and said second one of said two tubular conductive sections are configured as a cylinder, said first and second bases further configured as a cylinder.

12. The device of claim 11 further comprising:
    an insulating member disposed around the second one of said two tubular conductive sections.

13. The device of claim 12 further comprising:
a first and second joint located respectively at the first and second bases where the first and second bases respectively connect to the first and second ones of said two tubular conducting sections;
said insulating member extending in a distal direction beyond at least one of said first and second joints.

14. The device of claim 11 further comprising:
a first and second joint located respectively at the first and second bases where the first and second bases respectively connect to the first and second ones of said two tubular conducting sections;
said first and second joints formed by welding.

15. A medical coagulation instrument comprising:
a shaft having a distal end;
two electrode tips extending beyond the distal end of the shaft, said two electrode tips electrically insulated with respect to each other;
the electrode tips each having an inner surface and an outer surface, the inner surfaces facing a central longitudinal axis of the shaft and the outer surfaces facing opposite the inner surfaces;
the electrode tips each being a single piece;
at least one of said two electrode tips having a curved cross section such that at least one of the inner surface or the outer surface is curved;
a width measured between the inner surface and the outer surface of the at least one of said two electrode tips, the width increasing in a distal direction;
said shaft being hollow to define a channel extending along a longitudinal axis of the shaft and between said two electrode tips.

16. The medical coagulation instrument of claim 15 further comprising:
said two electrode tips being oriented such that an inner surface of each of said two electrode tips facing towards each other and an outer surface of each of said two electrode tips facing away from one another, at least one of said two electrode tips having a second curved cross section and a second curved surface.

17. The medical coagulation instrument of claim 15 wherein said two electrode tips are configured as thickening in the distal direction.

18. The medical coagulation instrument of claim 15 wherein the at least one of said two electrode tips are configured as widening conically in the distal direction.

19. The medical coagulation instrument of claim 15 wherein the distal end of at least one of said two electrode tips is configured as rounded.

20. The medical coagulation instrument of claim 15 further comprising:
said shaft including first and second conductive sections, the second conductive section arranged around the first conductive section such that an inner surface of the second conductive section is spaced apart from an outer surface of the first conductive section;
a first one of said two electrode tips connected to a first base;
a second one of said two electrode tips connected to a second base;
a proximal end of the first base connected to a distal end of the first conductive section;
a proximal end of the second base connected to a distal end of the second conductive section.

21. The medical coagulation instrument of claim 20 wherein the first and second bases are respectively connected to the first and second conductive sections by welding.

22. The medical coagulation instrument of claim 20 further comprising an insulating section disposed between the first and second conductive sections.

23. The medical coagulation instrument of claim 22 wherein said insulating section extends between the first and second bases.

24. The medical coagulation instrument of claim 15 wherein the curved cross section of the at least one of said two electrode tips is an arc less than a semicircle, the curved cross section being perpendicular to a longitudinal axis of the at least one of said two electrode tips.

* * * * *